(12) United States Patent
Lee et al.

(10) Patent No.: US 11,701,230 B2
(45) Date of Patent: Jul. 18, 2023

(54) PATIENT-SPECIFIC MANDIBULAR IMPLANT INSERTED INTO MANDIBULAR DEFECT REGION AND METHOD OF MANUFACTURING THE SAME

(71) Applicant: Medyssey Co., Ltd., Jecheon-si (KR)

(72) Inventors: Ui-Lyong Lee, Seoul (KR); Jong-Wuk Jang, Seoul (KR); Kwum-Mook Lim, Uijeongbu-si (KR); Su-Heon Woo, Uijeongbu-si (KR); Hyo-Bok Jeong, Jecheon-si (KR); Tae-Hyun Park, Jecheon-si (KR); Hyun-Woo Jung, Jecheon-si (KR)

(73) Assignee: MEDYSSEY CO., LTD., Jecheon-si (KR)

( * ) Notice: Subject to any disclaimer, the term of this patent is extended or adjusted under 35 U.S.C. 154(b) by 854 days.

(21) Appl. No.: 16/561,649

(22) Filed: Sep. 5, 2019

(65) Prior Publication Data

US 2020/0205984 A1    Jul. 2, 2020

(30) Foreign Application Priority Data

Dec. 26, 2018    (KR) .................. 10-2018-0169588

(51) Int. Cl.
*A61F 2/28*    (2006.01)
*B33Y 50/00*    (2015.01)
(Continued)

(52) U.S. Cl.
CPC .............. *A61F 2/2803* (2013.01); *A61B 6/14* (2013.01); *A61F 2/30942* (2013.01); *B33Y 50/00* (2014.12); *B33Y 80/00* (2014.12); *A61B 6/032* (2013.01); *A61F 2002/30948* (2013.01); *A61F 2002/30952* (2013.01); *A61F 2002/30985* (2013.01); *A61F 2310/00023* (2013.01)

(58) Field of Classification Search
CPC . A61F 2/2803; A61F 2/30942; A61F 2/30985
See application file for complete search history.

(56) References Cited

U.S. PATENT DOCUMENTS 5,306,149 A * 4/1994 Schmid ................ A61C 8/0031
433/173
5,306,150 A * 4/1994 Gittleman ............. A61F 2/3662
433/176

(Continued)

FOREIGN PATENT DOCUMENTS

JP         5942066 B2    6/2016
KR    10-2014-0113982 A    9/2014

(Continued)

*Primary Examiner* — Alvin J Stewart
(74) *Attorney, Agent, or Firm* — Rabin & Berdo, P.C.

(57) ABSTRACT

Disclosed is a patient-specific mandibular implant inserted into a mandibular defect region and a method of manufacturing the same, and more particularly, to a patient-specific mandibular implant inserted into a mandibular defect region, which can be easily and rapidly manufactured using personalized three-dimensional (3D) printing technology for a defect region, can provide an effect of preparing a later step for restoring a tooth in advance, and can be easily manufactured tooth restoration data based on the Korean standard database (DB), and a method of manufacturing the same.

1 Claim, 7 Drawing Sheets

(51) Int. Cl.
 *B33Y 80/00* (2015.01)
 *A61B 6/14* (2006.01)
 *A61F 2/30* (2006.01)
 *A61B 6/03* (2006.01)

(56) References Cited

U.S. PATENT DOCUMENTS

| | | | | |
|---|---|---|---|---|
| 5,769,637 | A * | 6/1998 | Morgan | A61F 2/2846 433/176 |
| 6,030,218 | A * | 2/2000 | Robinson | A61C 8/0031 433/173 |
| 6,328,765 | B1 * | 12/2001 | Hardwick | A61L 27/58 623/23.72 |
| 8,485,820 | B1 * | 7/2013 | Ali | A61K 6/878 433/173 |
| 8,888,485 | B2 * | 11/2014 | Ali | A61B 6/032 433/173 |
| 9,308,060 | B2 * | 4/2016 | Ali | A61B 6/14 |
| 9,649,178 | B2 * | 5/2017 | Ali | A61C 8/0027 |
| 9,861,482 | B2 * | 1/2018 | Boiangiu | A61F 2/2846 |
| 10,357,367 | B2 * | 7/2019 | Daniel | A61F 2/2803 |
| 10,675,385 | B2 * | 6/2020 | Barbas | A61F 2/30767 |
| 10,828,108 | B2 * | 11/2020 | Buck | A61B 17/00491 |
| 11,337,816 | B2 * | 5/2022 | Huang | A61F 2/2846 |
| 2005/0192675 | A1 * | 9/2005 | Robinson | A61C 8/0006 623/23.46 |
| 2007/0269769 | A1 * | 11/2007 | Marchesi | A61C 8/0006 433/215 |
| 2010/0256773 | A1 * | 10/2010 | Thijs | A61F 2/2803 427/2.24 |
| 2012/0271418 | A1 * | 10/2012 | Hollister | A61F 2/28 623/23.57 |
| 2012/0296441 | A1 * | 11/2012 | Mikhail | A61F 2/2803 623/23.63 |
| 2013/0164707 | A1 * | 6/2013 | Ali | A61K 6/878 433/173 |
| 2013/0236853 | A1 * | 9/2013 | Axelsson | A61C 8/0006 433/173 |
| 2016/0128834 | A1 * | 5/2016 | Yakir | A61F 2/2803 433/176 |
| 2016/0310278 | A1 * | 10/2016 | Kessler | A61C 8/0006 |
| 2017/0165072 | A1 * | 6/2017 | Peng | A61F 2/28 |
| 2017/0216033 | A1 * | 8/2017 | Daniel | A61F 2/2846 |
| 2017/0216034 | A1 * | 8/2017 | Daniel | A61F 2/2846 |
| 2017/0290645 | A1 * | 10/2017 | Rostami | A61C 8/0006 |
| 2017/0354503 | A1 * | 12/2017 | Larsen | A61F 2/2846 |
| 2018/0193530 | A1 * | 7/2018 | Barbas | A61F 2/2803 |
| 2018/0221153 | A1 * | 8/2018 | Daniel | A61F 2/2846 |
| 2019/0076251 | A1 * | 3/2019 | Daniel | A61F 2/2846 |
| 2019/0076252 | A1 * | 3/2019 | Karg | A61F 2/30771 |
| 2019/0290436 | A1 * | 9/2019 | Daniel | A61F 2/2803 |
| 2020/0289271 | A1 * | 9/2020 | Nedrud | A61F 2/2803 |
| 2020/0315662 | A1 * | 10/2020 | Adam | B33Y 80/00 |
| 2021/0113335 | A1 * | 4/2021 | Huang | A61F 2/0077 |

FOREIGN PATENT DOCUMENTS

| | | |
|---|---|---|
| KR | 10-1846847 B1 | 4/2018 |
| KR | 10-2018-0079297 A | 7/2018 |

* cited by examiner

PATIENT-SPECIFIC MANDIBULAR IMPLANT INSERTED INTO MANDIBULAR DEFECT REGION AND METHOD OF MANUFACTURING THE SAME

BACKGROUND OF THE INVENTION

Field of the Invention

The present invention relates to a patient-specific mandibular implant inserted into a mandibular defect region and a method of manufacturing the same, and more particularly, to a patient-specific mandibular implant inserted into a mandibular defect region, which can be easily and rapidly manufactured using personalized three-dimensional (3D) printing technology for a defect region, can provide an effect of preparing a later step for restoring a tooth in advance, and can be easily manufactured tooth restoration data based on the Korean standard database (DB), and a method of manufacturing the same.

Description of the Related Art

In the conventional general mandibular implant, a partially defect site is mostly connected to a temporomandible by means of a plate. At this time, where an edentulous jaw is existed in the mandibular defect region, since it has a structure in that a dental implant cannot be inserted, the masticatory function capable of chewing food is lost.

Also, in the case of most implant technologies of the defect mandible, since it has an anatomical shape capable of transforming by means of a clinician as a transform model of the conventional reconstruction plate, the implant capable of aesthetically replacing it is impossible.

In the end, when the edentulous jaw is existed in the mandibular defect region, since the dental implant cannot be inserted, the masticatory function capable of chewing food cannot help but be lost.

Accordingly, it requires a new mandibular implant for improving the above problem.

On the other hand, since the conventional technology on the mandible restoration is not a customized technology but ready-made technology, it cannot provide the patients with the appropriate implants.

Even if it would be a somewhat progressive technology, where it is unconcerned about a dental root, since a separate working should be performed on the body later on, it gives a pain to the patient, is difficult to process the solid body, and reduces the durability of the body. Also, since it is necessary to move the fixing part during the operation, it can give a pain to the patient and damage the surrounding bone to be combined.

On the other hand, it discloses a Patent Literature 1 as the prior art related to the present invention.

According to the Patent Literature 1, it relates to a producing method of a support for filling a bone defect and, more specifically, to a producing method of a support for filling a bone defect, comprising the following steps: cooling and pulverizing a bioabsorbable polymer and tricalcium phosphate as materials; and forming the bioabsorbable polymer and tricalcium phosphate using a three-dimensional printing.

PATENT LITERATURE

Patent Literature 1: Korean Patent Registration No. 10-1846847 (Apr. 3, 2018)

SUMMARY OF THE INVENTION

The present invention has been made in view of the above-mentioned problem, and provides a patient-specific mandibular implant inserted into a mandibular defect region and a method of manufacturing the same. It is a first object of the present invention to provide a patient-specific mandibular implant inserted into a mandibular defect region, in which a dental-root support or a dental-root hole is formed in a tooth junction region to treat a tooth defect.

It is a second object of the present invention to provide a patient-specific mandibular implant including a dental-root restoration section formed using 3D printing technology.

It is a third object of the present invention to provide a process of manufacturing a patient-specific mandibular implant to integrate 3D printing technology.

According to an aspect of the invention to achieve the object described above, there is provided a patient-specific implant inserted into a mandibular defect region according to an embodiment of the present invention includes a body (100) having an outer contour corresponding to a mandibular defect region, a first fixture (200) fixed to a first defect end formed at one end of the mandibular defect region, a second fixture (300) fixed to a second defect end formed at the other end of the mandibular defect region, and a dental-root restoration section (400) being corrected to restore a defective part corresponding to a tooth root in the body.

Preferably, the dental-root restoration section (400) is formed of a dental-root support (410) or a dental-root hole (420) only with respect to a mandible of a tooth junction region; the body (100) is made of titanium, and when the body is produced by a 3D printer, the body is produced by a method of melting and laminating a metal material using an additive manufacturing process in which a metal material is melted and then manufactured in the same manner as a generated image; the dental-root restoration section (400) is designed in consideration of the pressure applied during chewing between a defective tooth and an upper tooth; the dental-root restoration section (400) is 3D-printed based on a root of an opposite tooth that is not defective; the dental-root restoration section (400) is inclined at a certain angle from the horizontal plane so that upper and lower teeth are parallel and matched to each other, thereby preventing damage to the teeth during continuous chewing; in the 3D printing, when there is no opposite mandibular scan information, when there is no opposite tooth root information, or when a mandible of a deficient patient is completely lost, a new information extraction section acquires information on nationality, gender, and height of the patient, and extracts a defect region using a size, volume, and density of the mandible from a standard mandible DB for each nationality based on the acquired information; and the standard mandible DB for each nationality is a database made in consideration of a size, volume and density of a mandible for each country, and stores an average mandibular size, volume, and density according to gender or height for each nationality.

BRIEF DESCRIPTION OF THE DRAWINGS

The above and other objects, features and advantages of the present invention will be more apparent from the following detailed description taken in conjunction with the accompanying drawings, in which.

REFERENCE SIGNS LIST

100: body
200: first fixture
300: second fixture
400: dental-root restoration section

DETAILED DESCRIPTION OF THE PREFERRED EMBODIMENT

A patient-specific implant inserted into a mandibular defect region according to an embodiment of the present invention includes a body (100) having an outer contour corresponding to a mandibular defect region, a first fixture (200) fixed to a first defect end formed at one end of the mandibular defect region, a second fixture (300) fixed to a second defect end formed at the other end of the mandibular defect region, and a dental-root restoration section (400) being corrected to restore a defective part corresponding to a tooth root in the body.

The body (100) is made of a porous metal material.

The dental-root restoration section (400) is 3D-printed based on the root of an opposite tooth that is not defective.

The dental-root restoration section (400) is formed of a dental-root support (410) or a dental-root hole (420) only with respect to a mandible of a tooth junction region.

The dental-root restoration section (400) is designed in consideration of the pressure applied during chewing between a defective tooth and an upper tooth.

Meanwhile, a method of manufacturing a patient-specific implant inserted into a mandibular defect region includes a step of scanning a defective mandible with a 3D scanner (S100), a step of acquiring a clear and obvious 3D scan image through primary correction (S200), a step of estimating a defect region by referring to opposite mandibular scan information (S300), and a step of generating a dental-root support or dental-root hole image by referring to opposite tooth scan information only with respect to a mandible of a tooth junction region (S400).

Hereinafter, a patient-specific mandibular implant inserted into a mandibular defect region and a method of manufacturing the same according to the present invention will be described in detail with reference to the accompanying drawings.

Figure 1:
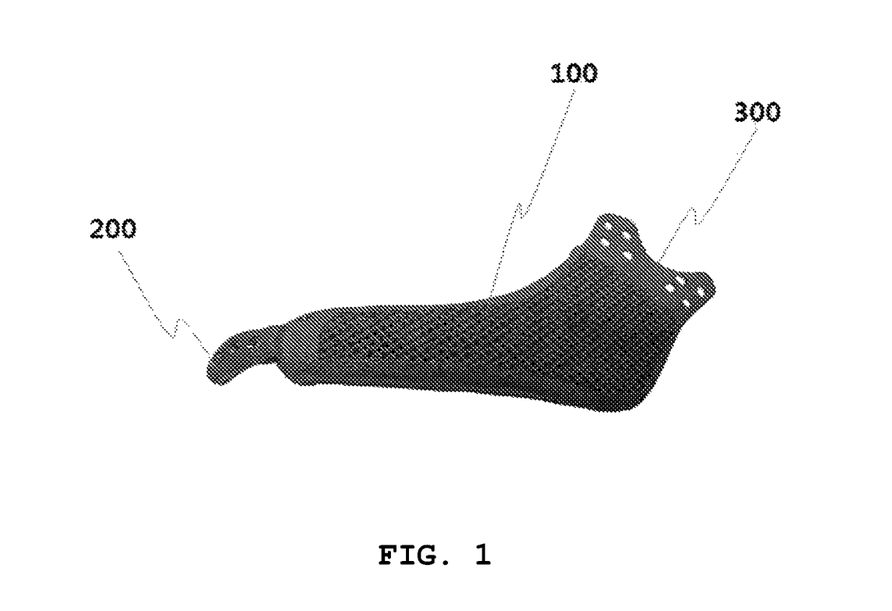
FIG. 1 is a basic configuration view illustrating a patient-specific mandibular implant inserted into a mandibular defect region according to an embodiment of the present invention.

FIG. 1 is a configuration view illustrating a patient-specific mandibular implant inserted into a mandibular defect region according to an embodiment of the present invention.

As illustrated in FIG. 1, the patient-specific mandibular implant inserted into a mandibular defect region includes a body (100), a first fixture (200), a second fixture (300), and a dental-root restoration section (400).

The patient-specific implant inserted into a mandibular defect region according to the present invention refers to a prosthesis that is implanted for a patient whose mandible is defective due to an accident or disease.

In particular, the present invention proposes a patient-specific implant prepared for restoring a root of a tooth in advance before treatment for a defect in the tooth only if the region of the tooth is damaged.

The body (100) has an outer contour corresponding to a mandibular defect region.

Figure 2:
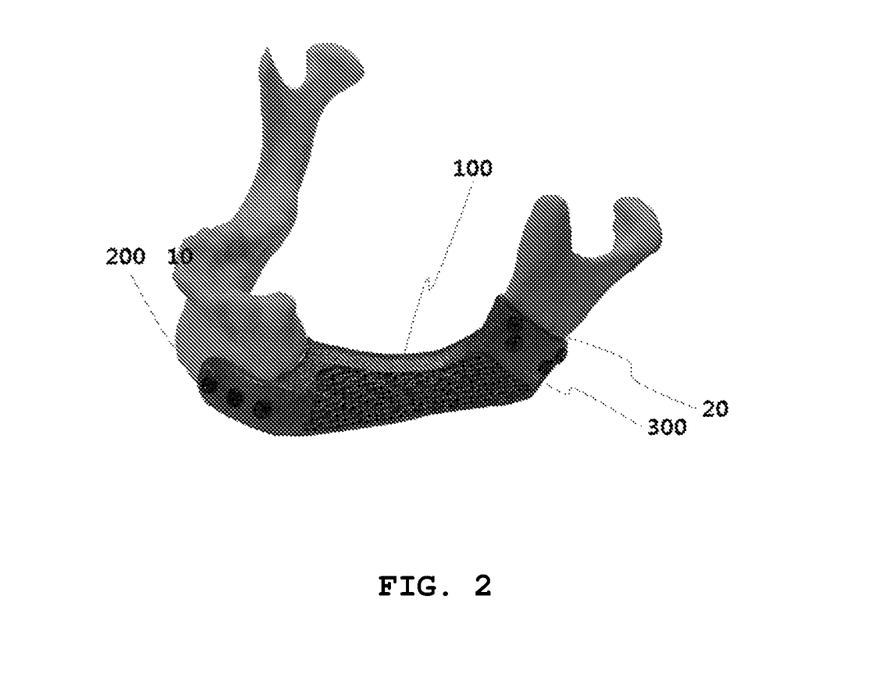
FIG. 2 is an example view illustrating a body which is formed to have an outer contour corresponding to a mandibular defect region between the left mandible and the right mandible in a patient-specific mandibular implant inserted into a mandibular defect region according to an embodiment of the present invention.

As illustrated in FIG. 2, the body (100) is formed to have an outer contour corresponding to the mandibular defect region between the left mandible and the right mandible.

That is, the body is inserted into a bone defect region and replaces a defective bone.

The body has a size and shape corresponding to the defective bone.

For example, the body may be 3D-printed by acquiring computed tomography (CT) information on the bone defect region, generating a body image to replace the defective bone based on the acquired information, and then printed based on the generated image.

The body may be made of metal.

For example, the body may be made of titanium. When the body is produced by a 3D printer, a method may be performed of melting and laminating a metal material using an additive manufacturing process in which a metal material is melted and then manufactured in the same manner as the generated image.

According to a preferred embodiment, the body (100) is made of a porous metal material.

That is, the implant has a porous structure by the porous material, so that the implant can be used for a long time without causing any complication since it is excellent in bonding strength with surrounding normal tissue.

The porous structure has the effect of increasing a bone fusion rate with the existing bone and reducing the weight of the implant.

According to the present invention, the implant having the size and shape corresponding to the bone defect region is stably inserted and fixed into the bone defect region to replace the defective bone, thereby minimizing patient discomfort.

Furthermore, since the implant is manufactured to fit the bone defect region within a short time, it is possible to minimize complications such as bleeding and infection by virtue of the shortening of operation time.

The first fixture (200) is fixed to a first defect end (10) formed at one end of the left mandibular defect region.

The first fixture (200) has holes formed at regular intervals, and is fixed to the first defect end by inserting a coupling means into a corresponding one of the holes.

The second fixture (300) is fixed to a second defect end (20) formed at the other end of the right mandibular defect region.

The second fixture (300) has holes formed at regular intervals, and is fixed to the second defect end by inserting a coupling means into a corresponding one of the holes.

For example, the body may be coupled and fastened to the bone defect region by a plate and screw or an intramedullary stem, as described above.

Meanwhile, the bone defect region of the human body includes a forearm, a humerus, a sacrum, a zygoma, a femur, a tibia, a fibula, a sternum, a scapula, and a calcaneus, but they are not exposed to the outside. Since the present invention relates to a mandible that supports teeth exposed to the outside, it is necessary to correct parts corresponding to the teeth.

That is, the mandibular defect region is usually a region combined with a tooth part, which is different from the bone defect regions that are other defect regions of the human body.

Accordingly, the dental-root restoration section (400) is corrected to restore a defective part corresponding to the tooth root in the body.

Figure 3:
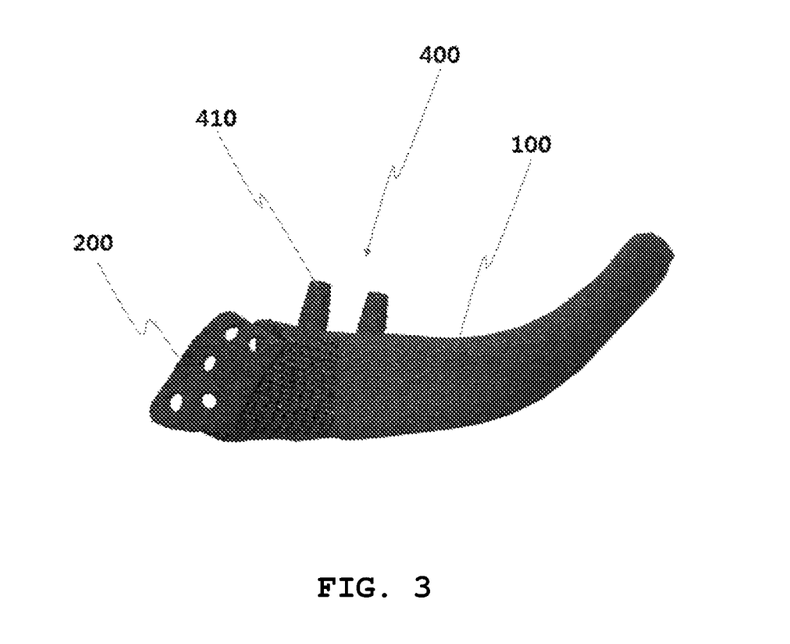
FIG. 3 and FIG. 4 are example views illustrating a dental-root support only with respect to a mandible of a tooth junction region in a patient-specific mandibular implant inserted into a mandibular defect region according to an embodiment of the present invention.
Figure 4:
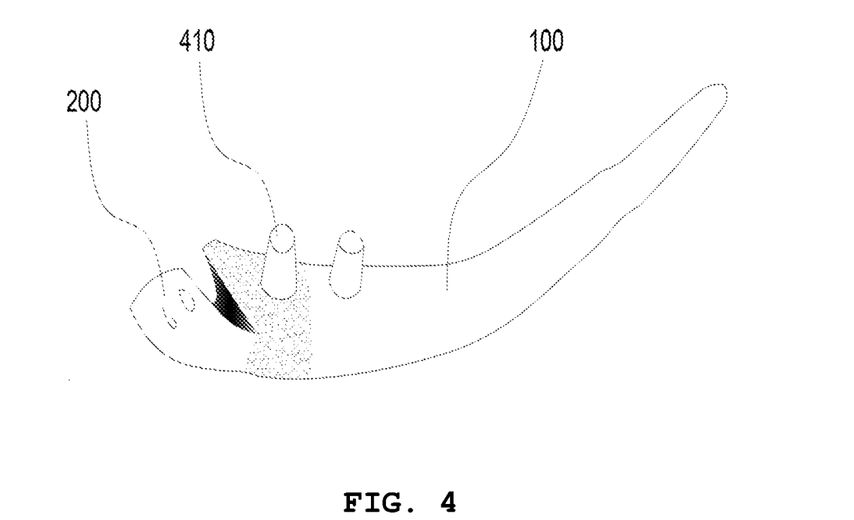

That is, as illustrated in FIGS. 3 and 4, the dental-root restoration section (400) is formed of a dental-root support (410) only with respect to a mandible of a tooth junction region.

In an example of the present invention, the dental-root support (410) consists of two dental-root supports.

Figure 5:
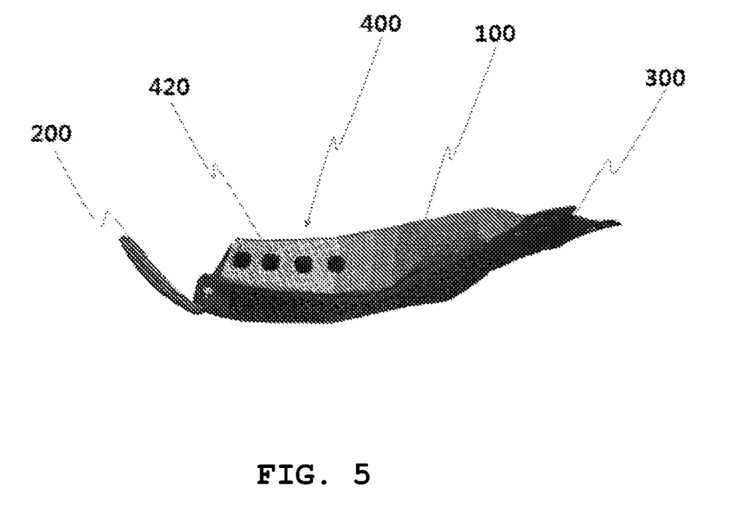
FIG. 5 is an example view illustrating a dental-root hole in a patient-specific mandibular implant inserted into a mandibular defect region according to an embodiment of the present invention.

Alternatively, the dental-root restoration section (400) is formed of a dental-root hole (420).

That is, as illustrated in FIG. 5, when the dental-root hole (420) consists of, for example, four dental-root holes, the dental implant may be placed later in a corresponding one of the dental-root holes.

Figure 6:
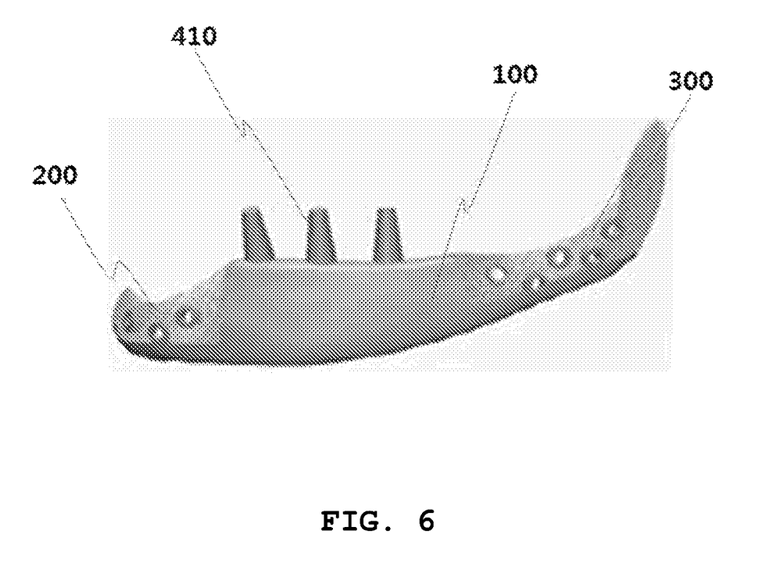
FIG. 6 is a configuration view illustrating a patient-specific mandibular implant inserted into a mandibular defect region according to an embodiment of the present invention.

In summary, the implant according to the most preferred embodiment of the present invention includes, as illustrated in FIG. 6, a body (100) having an outer contour corresponding to a mandibular defect region, a first fixture (200) fixed to a first defect end formed at one end of the mandibular defect region, a second fixture (300) fixed to a second defect end formed at the other end of the mandibular defect region, and a dental-root restoration section (400) corrected to restore a defective part corresponding to a tooth root in the body.

Figure 7:
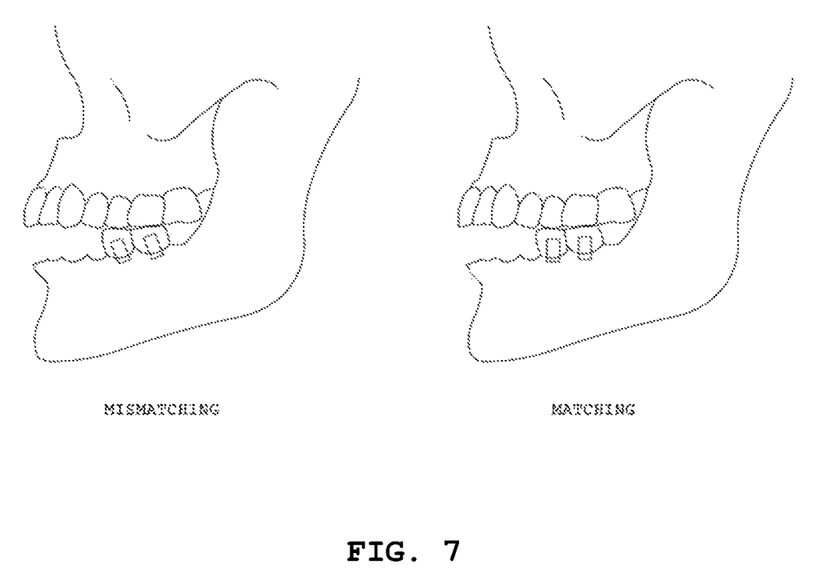
FIG. 7 through FIG. 9 are example views in that a dental-root restoration section is designed in consideration of the pressure applied during chewing between a defective tooth and an upper tooth in a patient-specific mandibular implant inserted into a mandibular defect region according to an embodiment of the present invention.
Figure 8:
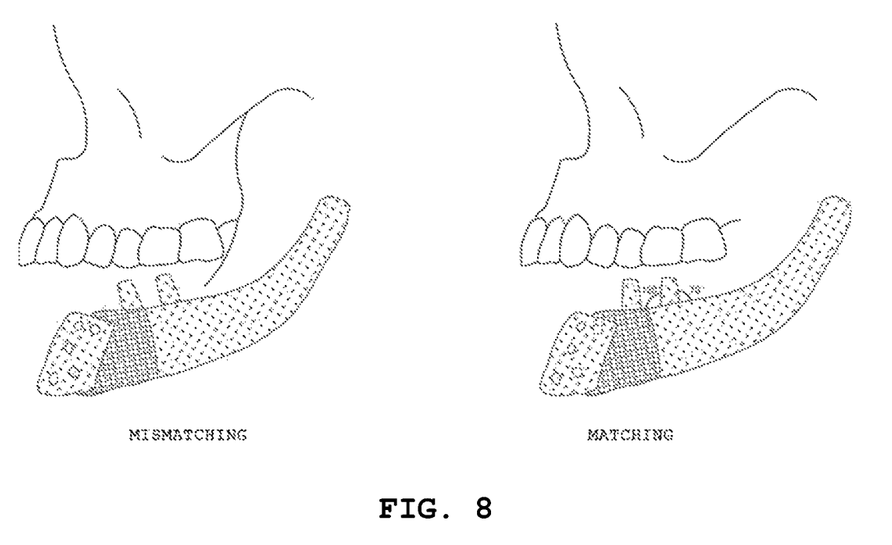
Figure 9:
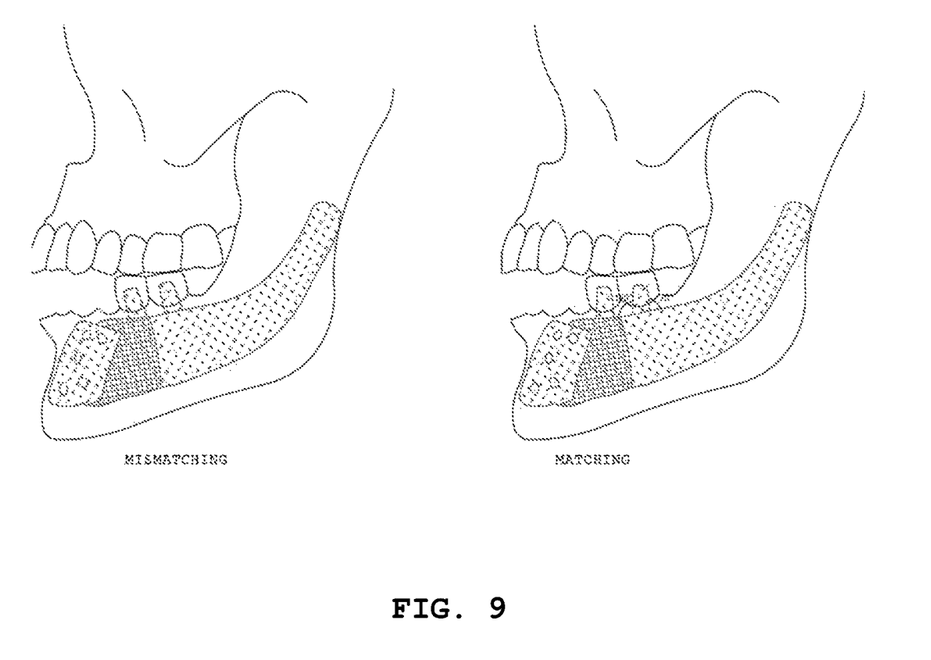

Meanwhile, as illustrated in FIGS. 7 to 9, the dental-root restoration section (400) is designed in consideration of the pressure applied during chewing between a defective tooth and an upper tooth.

For example, the dental-root restoration section (400) should be designed in consideration of an angle of 90 degrees in the direction in which the upper tooth moves down.

In other words, it is usually designed at an angle of 90 degrees about the mandible (jawbone), which may lead to mismatching.

As illustrated in FIG. 8, if the dental-root restoration section is formed perpendicular to the horizontal plane of the body as in the drawing, mismatching occurs because the upper tooth and the lower tooth are not horizontal, which may continuously damage the teeth during chewing.

Accordingly, as illustrated in the right drawings of FIGS. 8 and 9, when the dental-root restoration section is inclined at a certain angle from the horizontal plane, namely, when the left of the dental-root restoration section forms an angle of 120 degrees and the right thereof forms an angle of 70 degrees, the upper teeth and the lower teeth are parallel and matched to each other. Therefore, it is possible to solve the problem with damage to the teeth during chewing.

The dental-root restoration section (400) is 3D-printed based on the root of an opposite tooth that is not defective.

Figure 10:
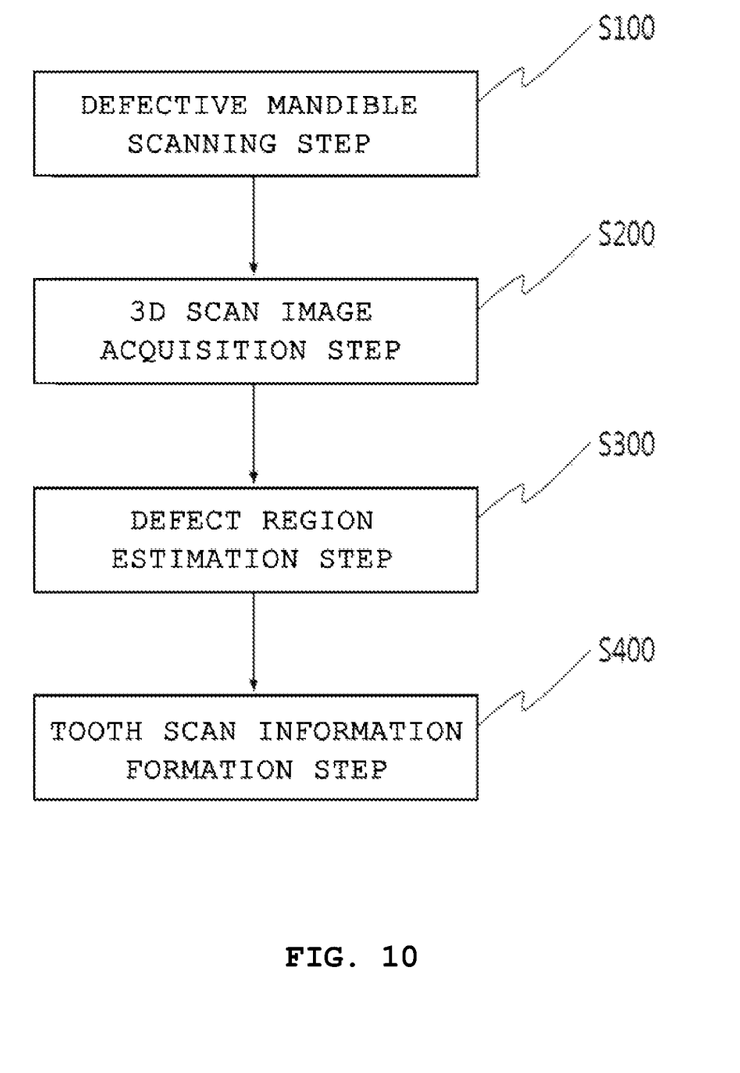
FIG. 10 is a flow chart illustrating a method of manufacturing a patient-specific implant inserted into a mandibular defect region according to an embodiment of the present invention.

As such, in order to perform the 3D printing, there is provided a method of manufacturing a patient-specific implant inserted into a mandibular defect region according to an embodiment of the present invention, as illustrated in FIG. 10. The method includes a step of scanning a defective mandible with a 3D scanner (S100), a step of acquiring a clear and obvious 3D scan image through primary correction (S200), a step of estimating a defect region by referring to opposite mandibular scan information (S300), and a step of generating a dental-root support or dental-root hole image by referring to opposite tooth scan information only with respect to a mandible of a tooth junction region (S400).

In more detail, referring to FIG. 10, the defective mandible is scanned with the 3D scanner (S100).

Next, the clear and obvious 3D scan image is acquired through the primary correction (S200).

In the primary correction, the 3D scan image is acquired clearly and obviously using a typical correction algorithm.

Next, the defect region is estimated by referring to the opposite mandibular scan information (S300).

That is, after an image on the opposite mandible is acquired using the 3D scanner, the defect region is estimated based on the symmetry of the acquired image.

Next, when the defect region corresponds to the tooth junction region, the dental-root support or dental-root hole image is generated by referring to the opposite tooth scan information only with respect to the mandible of the tooth junction region (S400).

In addition, the dental-root support or dental-root hole image is generated based on the opposite tooth scan information.

Next, the generated 3D image is printed using a 3D printer.

Figure 11:
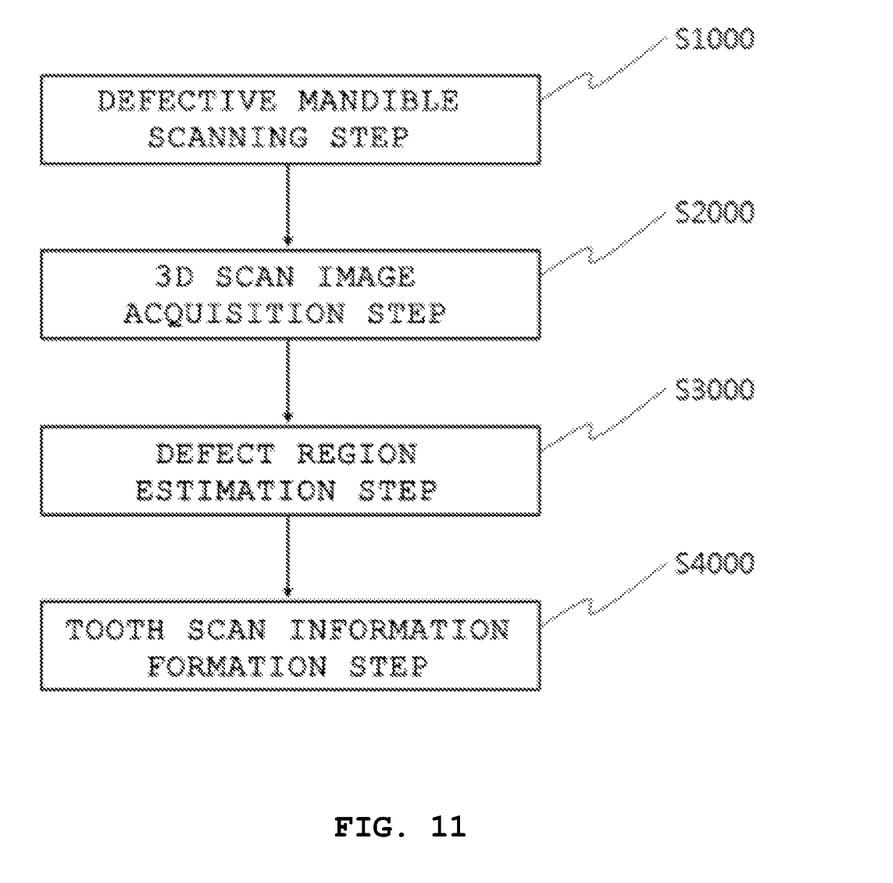
FIG. 11 is a flow chart illustrating a method of manufacturing a patient-specific implant inserted into a mandibular defect region according to another embodiment of the present invention.

Meanwhile, as illustrated in FIG. 11, a method of manufacturing a patient-specific implant inserted into a mandibular defect region according to another embodiment of the present invention includes a step of scanning a defective mandible with a 3D scanner (S1000), a step of acquiring a clear and obvious 3D scan image through primary correction (S2000), a step of estimating a defect region by first referring to opposite mandibular scan information and, when there is no opposite mandibular scan information, estimating the defect region by referring to a standard mandible DB for each nationality (S3000), and a step of generating a dental-root support or dental-root hole image by referring to opposite tooth scan information only with respect to a mandible of a tooth junction region (S4000).

In more detail, the defective mandible is scanned with the 3D scanner (S1000).

Next, the clear and obvious 3D scan image is acquired through the primary correction (S2000). Then, the defect region is estimated, first by referring to the opposite mandibular scan information. In the case when there is no opposite mandibular scan information, the defect region is estimated by referring to the standard mandible DB for each nationality (S3000).

That is, in estimating the defect region, it is possible to acquire the most accurate scan information by first referring to the mandibular scan information opposite thereto.

However, if the opposite mandibular scan information cannot be obtained due to the opposite mandible also being defective, the defect region is estimated by referring to the standard mandible DB for each nationality.

The standard mandible DB for each nationality described above is a database made in consideration of the size, volume and density of a mandible for each country. In the case of Koreans, the average mandibular size, volume, and density of Koreans are statistically recorded in the standard mandible DB.

For example, the average mandibular size, volume, and density of Koreans will vary depending on the gender or the height, and the standard mandible DB for each nationality is to obtain and store the data for them.

Meanwhile, in order to analyze the size, volume, and density of a mandible for each nationality in consideration of the gender or the height, the present invention may further include a CNN learning section for acquiring thousands to tens of thousands of mandibular images for each nationality, extracting feature points, and learning them using a CNN neural network to estimate the size, volume, and density of a mandible for each nationality.

Thus, the mandible for each nationality is learned through the CNN learning section, and a result value for the learning is stored.

In addition, the present invention may further include a new information extraction section for acquiring information on the nationality, gender, and height of a new deficient patient whose mandible is completely lost, and extracting the size, volume, and density of the mandible based on the acquired information.

Next, the dental-root support or dental-root hole image is generated by referring to the opposite tooth scan information only with respect to the mandible of the tooth junction region (S4000).

According to the present invention, there is an effect in that it provides a patient-specific mandibular implant inserted into a mandibular defect region, in which a dental-root support or a dental-root hole is formed in a tooth junction region to treat a tooth defect.

In addition, there is another effect in that it provides a patient-specific mandibular implant including a dental-root restoration section formed using 3D printing technology.

In addition, there is further another effect in that it provides a process of manufacturing a patient-specific mandibular implant to integrate 3D printing technology.

That is, it can be easily and rapidly manufactured using personalized three-dimensional (3D) printing technology for a defect region, can provide an effect of preparing a later step for restoring a tooth in advance, and can be easily manufactured tooth restoration data based on the Korean standard database (DB), and a method of manufacturing the same.

While the present invention has been described with respect to the specific embodiments, it will be apparent to those skilled in the art that various changes and modifications may be made without departing from the spirit and scope of the invention as defined in the following claims.

What is claimed is:

1. A patient-specific implant configured to be inserted into a mandibular defect region of a patient, comprising:

a body (100) having an outer contour corresponding to the mandibular defect region and made of a porous metal material;

a first fixture (200) configured to be fixed to a first defect end formed at one end of the mandibular defect region;

a second fixture (300) configured to be fixed to a second defect end formed at another end of the mandibular defect region; and a dental-root restoration section (400) corrected to restore a defective part corresponding to a tooth root in the body, wherein:

the dental-root restoration section (400) is formed of a dental-root support (410) or a dental-root hole (420) only with respect to a mandible of a tooth junction region of the patient;

the body (100) is made of titanium, and when the body is produced by a 3D printer, the body is produced by a method of melting and laminating a metal material using an additive manufacturing process in which a metal material is melted and then manufactured in a same manner as a generated image;

the dental-root restoration section (400) is designed in consideration of a pressure applied during chewing between a defective tooth and an upper tooth of the patient;

the dental-root restoration section (400) is 3D-printed based on a root of an opposite tooth that is not defective;

the dental-root restoration section (400) is inclined at a certain angle from a horizontal plane so that upper and lower teeth of the patient are parallel and matched to each other, thereby preventing damage to the upper and lower teeth during continuous chewing;

in the 3D printing, when there is no opposite mandibular scan information, when there is no opposite tooth root information, or when a mandible of a deficient patient is completely lost, a new information extraction section acquires information on nationality, gender, and height of the patient, and extracts a defect region using a size, volume, and density of the mandible from a standard mandible database (DB) for each nationality based on the acquired information; and the standard mandible DB for each nationality is a database made in consideration of a size, volume and density of a mandible for each country, and stores an average mandibular size, volume, and density according to gender or height for each nationality;

wherein the first fixture (200) and the second fixture (300) are formed as flaps or flanges each having holes formed at regular intervals, the first fixture (200) and the second fixture (300) projecting respectively from a first end of the body, the first end of the body corresponding to the first defect end, and a second end of the body, the second end of the body corresponding to the second defect end;

the first fixture (200) is configured to extend beyond the first end of the body; and the second fixture (300) is deformable and attachable as a partial sleeve partly encircling the second defect end formed at the other end of the mandibular defect region.

* * * * *